United States Patent [19]

Clapot et al.

[11] 4,099,955
[45] Jul. 11, 1978

[54] PLANT REGULATING COMPOUNDS

[75] Inventors: Claude Clapot, Oullins; Jean Vial, Tassin; Louis Dumont, Chaponost, all of France

[73] Assignee: Philagro, Lyons, France

[21] Appl. No.: 734,172

[22] Filed: Oct. 20, 1976

Related U.S. Application Data

[60] Continuation-in-part of Ser. No. 472,471, May 22, 1974, Pat. No. 3,990,883, which is a division of Ser. No. 725,295, Sep. 21, 1976.

[30] Foreign Application Priority Data

May 22, 1973 [FR] France .................. 73 19579

[51] Int. Cl.² ............................................. A01N 9/12
[52] U.S. Cl. ................................................ 71/98; 71/76
[58] Field of Search ..................... 260/465 D, 465.5 R; 71/98, 105

[56] References Cited

U.S. PATENT DOCUMENTS

| 3,020,144 | 2/1962 | Gobeil et al. | 260/465 D |
| 3,668,217 | 6/1972 | Fujinami et al. | 260/465 D |
| 3,698,887 | 10/1972 | Chupp | 71/120 |
| 3,965,139 | 6/1976 | Scozzie | 71/105 |
| 3,978,123 | 8/1976 | Chan | 71/98 |

FOREIGN PATENT DOCUMENTS 430,323  8/1967  Switzerland ................... 71/98

*Primary Examiner*—Glennon H. Hollrah
*Attorney, Agent, or Firm*—Browdy & Neimark

[57] ABSTRACT

Compounds having an effect on modifying the physiology of plants in various ways have the formula

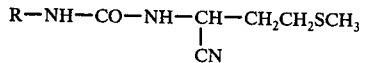

wherein R is H, alkyl, halogenated alkyl, cycloalkyl, naphthyl, phenyl or halogenated phenyl, and R is preferably alkyl of 2–5 carbons, naphthyl, phenyl or chlorinated phenyl.

12 Claims, No Drawings

PLANT REGULATING COMPOUNDS

FIELD OF INVENTION

This is a continuation-in-part of application Ser. No. 472,471 filed May 22, 1974, now U.S. Pat. No. 3,990,883, and of its divisional application Ser. No. 725,295 filed Sept. 21, 1976, the contents of which are hereby incorporated by reference.

This invention relates to a new cyano-urea derivatives of methionine and to compositions thereof with plant-growth regulating properties.

BACKGROUND

The term "growth regulator" is used in its accepted sense in the French language, which corresponds to "growth substance" in Anglo-Saxon literature, the term "growth" relating to the production of living matter and not simply to the modification of the size of plants. Accordingly, growth regulators in the context of the invention are compounds which are capable of modifying the physiology of plants in various different ways.

It has already been proposed (cf. Belgian Pat. No. 782,037) to use methionine and certain of its esters as growth regulators. Unfortunately, compounds of this kind are often not effective enough for commercial application.

SUMMARY

The present invention relates to other compounds of methionine which correspond to the following general formula:

$$R-\underset{R_1}{\underset{|}{N}}-\underset{}{\overset{X}{\overset{\|}{C}}}-\underset{R_2}{\underset{|}{N}}-\underset{R_3}{\underset{|}{\overset{R_4}{\overset{|}{C}}}}-CH_2-CH_2-S-CH_3 \quad (I)$$

In the above formula:

R represents hydrogen, an alkyl radical, a halogenated alkyl radical, a cycloalkyl radical, an optionally substituted aryl radical, an optionally substituted aralkyl radical, an acyl or aroyl radical, an optionally substituted heterocycle, the alkyl portion preferably containing 1 to 5 carbon atoms;

$R_1$ and $R_3$, which may be the same or different, represent hydrogen, an alkyl radical containing 1 to 5 carbon atoms;

$R_2$ represents hydrogen, alkyl (optionally halogenated or substituted by a hydroxyl), formyl, acyl, carbamoyl monosubstituted or disubstituted on the nitrogen;

$R_4$ is nitrile;

X represents oxygen or sulphur.

DETAILED DESCRIPTION OF EMBODIMENTS

Of particular interest are the compounds according to the invention which correspond to the formula:

$$R-NH-CO-NH-\underset{CN}{\underset{|}{CH}}-CH_2CH_2SCH_3 \quad (II)$$

where R represents hydrogen, an alkyl radical, a halogenated alkyl radical, a cycloalkyl radical, a naphthyl radical, an optionally substituted aryl radical of the formula in which A represents hydrogen or halogen, B represents hydrogen, halogen, an alky, alkoxy, $NO_2$, CN, $CF_3$, COOR′ where R′ represents hydrogen or alkyl;

m is an integer from 0 to 5, n is an integer from 0 to 3, m and n together being at most equal to 5;

an optionally substituted aralkyl radical, an acyl radical, aroyl radical or an optionally substituted heterocycle; the alkyl part of the radicals containing from 1 to 5 carbon atoms; and more particularly compounds of formula II wherein R is alkyl of 1 – 5 carbons, naphthyl, phenyl or chlorinated phenyl.

Within the preferred sub-genus of formula II, those compounds particularly preferred are the phenylureas $$\underset{B_n}{\underset{A_m}{\phantom{X}}}-NH-CO-NH-\underset{CN}{\underset{|}{CH}}-CH_2CH_2SCH_3 \quad (III)$$

wherein A and B are hydrogen or chlorine.

The compounds of formula (I) in which $R_4$ is a nitrile radical are synthetizised by a process of the kind commonly used, by reacting an alkyl-, aryl or aralkyl (thio) isocyanate with 2-amino 4-methylthiobutyronitrile in accordance with the following scheme:

$$R-N=C=O + H_2N-\underset{CN}{\underset{|}{CH}}-CH_2-CH_2-SCH_3 \longrightarrow$$

$$R-NH-\underset{O}{\overset{\|}{C}}-NH-\underset{CN}{\underset{|}{CH}}-CH_2-CH_2-S-CH_3$$

The isocyanate, in solution in an inert solvent, for example benzene, is poured dropwise with stirring into a solution in benzene of 2-amino 4-methylthiobutyronitrile, the medium being cooled to maintain a temperature at most equal to 30° C.

After about half an hour, the desired product begins to precipitate. Then, when it is completely cooled, it is filtered, centrifuged, washed and dried.

The following compounds were prepared by this process:

63 - (DL) N-methyl - N′ - (I-cyano, 3 methylthio)-propylurea

64 - (DL) N-phenyl-N′ - (I-cyano, 3 methylthio) propylurea

65 - (DL) N 3,5 dichlorophenyl-N′ (I-cyano, 3 methylthio) propylurea

66 - (DL) N 3,4 dichlorophenyl-N′ (I-cyano, 3 methylthio) propylurea

67 - (DL) N- (α naphthyl) N′ (I-cyano, 3 methylthio) propylurea

The following examples, offered without limitation, illustrate the preparation of the compounds according to the invention and their plant-growth regulating properties.

EXAMPLE 63

Preparation of N-methyl, N' (I-cyano, 3 methylthio) propylurea

A solution of 2.85 g (0.05 mole) of methylisocyanate in benzene is added dropwise to a solution of 0.5 g (0.05 mole) of 2-amino 4-butyronitrile. The temperature is maintained under 30° C during this time. After half an hour of contact, the desired compound begins to precipitate. When it is completely cooled, it is centrifuged, washed and dried. It is then recrystallized in ethyl acetate.

Yield: 84%
Melting point: 107° C

| Centesimal analysis for $C_7H_{13}N_3OS$ | | |
|---|---|---|
| | C % | H % | N % |
| Calculated | 44.91 | 6.96 | 22.45 |
| Found | 45.05 | 6.98 | 22.40 |

EXAMPLES 64 TO 67

The procedure is the same as the preceding example, but using a suitable isocyanate. The characteristics of the compounds obtained and their yields are set out in the following table:

$$R-NH-CO-NH-\underset{CN}{CH}-CH_2-CH_2SCH_3$$

| Compound No. | R | Empirical formula | MW | Physical constants | Yield | | Centesimal analysis | | |
|---|---|---|---|---|---|---|---|---|---|
| | | | | | | | C% | H% | N% |
| 63 | $CH_3-$ | $C_7H_{13}N_3OS$ | 187 | m.p. 107° C | 83.5% | C: | 44.91 | 6.96 | 22.45 |
| | | | | | | F: | 45.05 | 6.98 | 22.40 |
| 64 | 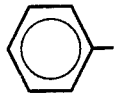 | $C_{12}H_{15}N_3OS$ | 249 | m.p. 114.5° C | 77 % | C: | 57.83 | 6.02 | 16.87 |
| | | | | | | F: | 57.58 | 6.10 | 16.69 |
| 65 | 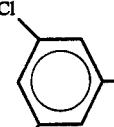 | $C_{12}H_{13}Cl_2N_3OS$ | 318 | m.p. 119° C | 79 % | C: | 45.28 | 4.09 | 13.21 |
| | | | | | | F: | 45.14 | 4.17 | 13.19 |
| 66 | 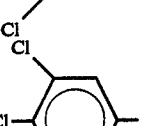 | $C_{12}H_{13}Cl_2N_3OS$ | 318 | m.p. 134.5° C | 69 % | C: | 45.28 | 4.09 | 13.21 |
| | | | | | | F: | 45.12 | 4.12 | 13.47 |
| 67 | 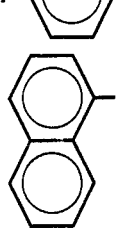 | $C_{16}H_{17}N_3OS$ | 299 | m.p. 131° C | 74.5 % | C: | 64.21 | 5.69 | 14.05 |
| | | | | | | F: | 64.28 | 5.74 | 14.41 |

The biological properties of the compounds according to the invention were demonstrated by tests in which the plants were treated by various methods depending essentially upon the type of plants tested and by the expected responses.

The term "solution" as used in the following relates either to an aqueous solution, where the active material is soluble in water, or, in the opposite case, an aqueous dispersion of a wettable powder containing 20% of the active material or a concentrated emulsion containing 10 g/l. of active material.

In a first method, the leaves of plants, such as green beans, or trees, e.g. olive, are treated by spraying with a solution containing 0.001 to 10 g/l of the material to be tested. The biometric and morphological development of the plants with respect to the untreated controls is then noted after 8 days, 25 days, 1 month. This method is used for the following tests bearing on the reduction in size and yield in fruit for beans and the dropping rate of olives.

According to a second method, the excision or "dropping" power of the compounds of the invention on plants such as the green bean, Contender variety, is evaluated by cutting the stem of the bean at the level of the pot, also cutting the leafstalks at 2 cm. from the stem and submerging the so-cut stem with its shortened leafstalks into a flanged tube containing a nutritive solution and the compound to be tested, for the concentrations in active material going from 0.001 to 10 g/l. The flanged tubes support the cut samples in vertical position. Each day, starting with the second day, the natural drop of the shortened leafstalks is noted and compared to a non-treated control.

According to a third method, the action of the compounds of the present invention in advancing maturation of green fruit is evaluated. For this test the selected green fruit, taken at the same level of the plant, are submerged for a determined duration in a solution containing from 0.1 to 10 g/l of the material to be tested. The changes in coloration of the fruit tested with respect to the non-treated controls are then observed.

In using these methods, there is observed in the following examples several modes of action of the products according to the invention on the growth of the plants treated.

I - Reduction of the Size on Contender Variety of Green Bean

The bean plants were sprayed at the stage of 2-4 leaves and the morphologic evolution of the beans up to the stage of maturation of the fruit was observed. The size of the overhead parts and the distances between nodes of the treated plants with respect to the non-treated controls were measured. Under these conditions, the product of Example 63 entails a diminution of the size of the plants of about 10% with respect to the control, for a dose of $10^{-4}$ mole/l, i.e. about 0.018 g/l. The products of Examples 64–67 have no obvious action.

II - Abscission (Dropping) of the Leaves on Contender Variety of Beans

There is observed at what moment is produced the leaf stalk fall in the case of the treated plants with respect to the fall of the leafstalks of the non-treated controls. Under these conditions, it is observed that a concentration of $10^{-4}$ mole/l, the compounds of Examples 64, 65, 66 and 67 have a very elevated abscission action because they cause the drop of the leafstalks after two days against ten days for the non-treated control. At a dose of $10^{-4}$ mole/l, the compound of Example 63 has a very elevated anti-abscission action since the fall of the leafstalks takes place only after an additional ten days have elapsed compared to that of the non-treated control.

In this new test, the abscission is the result of the breaking down of the links between the stem and the leaf stalk. As pointed out in the description of the test, the leaves are previously cut off in order to have more comparative results: from the biologist's points of view, each leaf can act as a supplementary source of food for each leaf stalk, and, when the leaves are not previously cut off, the results depend on the size of each leaf. It is worth noting that in nature, when the links between the stem and the leaf stalk are broken down, both the leaf stalk and the leaf fall down together.

The purpose of this test is to study how the present compounds can accelerate (Ex. 64 to 67) or delay (Ex. 63) the falling down of the leafstalks and consequently of the leaves. The comparative bean sample is subjected to the same succession of operations (cutting of the stem, etc.) but in this case the tube does not contain any growth regulating substance. By operating in this way, the leafstalks of the comparative bean sample fall down after about ten days, the leafstalks of the beans treated with compounds 64 to 67 after only two days, the leafstalks of the beans treated with compound 63 after about twenty days (i.e., for compound 63 about ten days after the falling down of the leafstalks of the untreated beans).

III - Yield of Fruit on Contender Variety of Bean

The number of the pounds of fruit formed is noted and compared to the non-treated control specimen. The following table indicated, for each of the compounds, at different doses, the variations of weight and the number of fruits of the treated plants with respect to the non-treated plants.

TABLE I

|  | Dose in mole/liter | Variation of weights | Variation of Number |
|---|---|---|---|
| Example 63 | $10^{-4}$ to $10^{-6}$ | + 20 % | − 10 % |
| Example 64 | $10^{-4}$ to $10^{-6}$ | + 44 % | − 30 % |
| Example 65 | $10^{-4}$ | + 12 % | + 33 % |
|  | $10^{-5}$ | + 6 % | + 25 % |
|  | $10^{-6}$ | − 14 % | + 33 % |
| Example 66 | $10^{-4}$ | + 4 % | + 15 % |
|  | $10^{-5}$ | + 17 % | + 46 % |
|  | $10^{-6}$ | + 20 % | + 54 % |
| Example 67 | $10^{-4}$ | + 10 % | − 30 % |

IV - Action on the Maturation of Montfavet Variety of Tomato

Green tomatoes are wetted for fifteen seconds in a solution of the products to be tested, a control being reserved for comparison.

Under these conditions, it is observed that whereas the controls remain green, the products of Examples 65 and 67 involve a maturation of about 50% for a concentration of active material of $1 \times 10^{-3}$ mole/l.

V - Abscission Action on Olives in the Open Air

There is applied onto the foliage of olive trees, of Moraiolo variety, a solution containing from 1 - 10 g/l of active material at the rate of 5 - 10 liters of solution per tree. This treatment is effected twenty days before the foreseen date for the harvest. Twenty days after the treatment, the number of naturally fallen olives and the number of fallen olives with mechanical vibration are counted and compared to the results obtained in the use of non-treated olive trees.

In the following table, N indicates the weight in kg of the olives on the tree at the time of treatment, CN, VM and M indicate respectively, at the moment of the harvest, the weight in kg of naturally fallen olives, by mechanical vibration and the olives remaining to pick by hand on the tree. Percentages are indicated below each weight figure.

TABLE II

|  | Dose of active material | CN | VM | CN + VM | M | N CN + VM + M |
|---|---|---|---|---|---|---|
| Example 65 | 3 g/l | 29.0 (19%) | 97.1 (64%) | 126.1 (83%) | 24.85 (17%) | 150.95 (100%) |
|  | 5 g/l | 34.0 (23%) | 102.3 (67%) | 136.3 (90%) | 14.85 (10%) | 151.15 (100%) |
| Comparison | 0 | 7.3 (6%) | 66.9 (52%) | 74.2 (58%) | 55.36 (42%) | 129.56 (100%) |

For the doses used, the defoliation remains very slight and is acceptable.

Further, open air trials have shown that some compounds according to the invention when used on cotton increase the number of capsules up to 50% and floral induction up to 40%. Other compounds as noted above have been found very effective to get a gathered fall of olives which facilitates the gathering very much.

These examples clearly demonstrate the remarkable properties of the compounds according to the invention which can thus be used in any type of plant, for example in large-scale cultivation, intensive cultivation, in cereals, fruits, vegetables, ornamental plants, medicinal plants and perfume plants with a view to increasing productivity, facilitating harvest, for example by abscission of leaves, accelerating the ripening of fruit, promoting branching, modifying habit, producing floral induction (flowering), retarding flowering to prevent frost damage, reducing size to obtain more compact plants, etc.

The doses in which the compounds according to the invention can be used vary within wide limits depending upon the required effect, upon the type of plant and its stage of treatment, upon the soil and climatic conditions. In general, doses of from 0.001 to 10 g/l are adequate, preferably 0.1 to 10 g/l.

In practice, the compounds according to the invention are rarely used on their own. More often, they are an integral part of formulations which generally comprise an inert agricultural support and/or a surfactant and/or other active agent(s) such as fertilizers, pesticides and/or fungicides, in addition to one or more (in admixture) of the active materials according to the invention.

In the context of the invention, a support is an organic or mineral, natural or synthetic material with which the active material is associated to facilitate its application to the plant, to seeds or to soil, or its transportation or handling. The support can be solid (clays, natural or synthetic silicates, resins, waxes, solid fertilizers) or fluid (water, alcohols, ketones, petroleum fractions, chlorinated hydrocarbons, liquefied gases).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions according to the invention can be prepared in the form of wettable powders, powders for dusting, granulates, solutions, emulsifiable concentrates, emulsions, suspended concentrates and aerosols.

The wettable powders according to the invention can be prepared in such a way that they contain from 20 to 95% by weight of active material, and they normally contain, in addition to a solid support, from 0 to 5% of a wetting agent, from 3 to 10% by weight of a dispersant and, when necessary, from 0 to 10% by weight of one or more stabilizers and/or other additives, such as penetration agents, adhesives or antilumping agents, colorants, etc.

One example of the composition of a wettable powder is given below, the percentages being expressed in weight:

| | |
|---|---|
| active material | 50 % |
| calcium lignosulphate (deflocculant) | 5 % |
| isopropylnaphthalene sulphonate (wetting agent) | 1 % |
| anti-lumping silica | 5 % |
| filler (kaolin) | 39 % |

The emulsifiable concentrates which can be applied by spraying generally contain, in addition to the solvent and, when necessary, a co-solvent, from 10 to 50% by weight/volume of active material, from 2 to 20% by weight/volume of suitable additives, such as stabilizers, penetration agents, corrosion inhibitors, colorants and adhesives.

The suspended concentrates which can also be applied by spraying are prepared in such a way that a fluid, stable non-sedimenting product is obtained, and they normally contain from 10 to 75% by weight of active material, from 0.5 to 15% by weight of surfactants, from 0.1 to 10% by weight of antisedimentation agents, such as protective colloids and thixotropic agents, from 0 to 10% by weight of suitable additives, such as antifoam agents, corrosion inhibitors, stabilizers, penetration agents and adhesives, and as support water or an organic liquid in which the active material is substantially insoluble. Certain solid organic materials or mineral salts can be dissolved in the support to assist in preventing sedimentation or as antifreeze agents for water.

Aqueous dispersions and emulsions, for example compositions obtained by diluting a wettable powder or an emulsifiable concentrate according to the invention with water, are included within the general scope of the invention. These emulsions can be of water-in-oil type or of the oil-in-water type, and can have a thick consistency resembling that of a "mayonnaise".

The compositions according to the invention can contain other ingredients, for example protective colloids, adhesives or thickeners, thixotropic agents, stabilizers or sequestrants, and other active materials known to exhibit pesticidal properties, in particular insecticides, fungicides or other growth regulators.

All these compositions can be applied to the plants by various methods, such as by spraying onto the aerial part of the plants, by soaking seeds, plants, clods, roots or fruit, by spraying the soil, by injecting the plant, etc.

It will be obvious to those skilled in the art that various changes may be made without departing from the scope of the invention and the invention is not to be considered limited to what is described in the specification.

What is claimed is:

1. A composition for plant growth regulation comprising an inert agricutural carrier and an amount sufficient to regulate plant growth of a compound of the formula

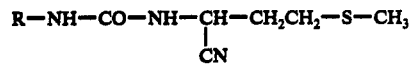

wherein R is H, alkyl of 1-5 carbons naphthyl, phenyl or chlorinated phenyl with the proviso that R is not 3,5-dichlorophenyl.

2. A composition in accordance with claim 1 wherein R is phenyl or chlorinated phenyl.

3. A composition in accordance with claim 1 wherein R is phenyl; or 3,4-dichlorophenyl.

4. A composition in accordance with claim 1 wherein said compound is selected from the group consisting of N-methyl-N'-(1-cyano-3-methylthio) propylurea; N-phenyl-N'-(1-cyano-3-methylthio) propylurea; N-3,4-dichlorophenyl-N'-(1-cyano-3-methylthio) propylurea; and N-(α-naphthyl)-N'-(1-cyano-3-methylthio) propylurea.

5. A composition in accordance with claim 1 wherein said compound is N-methyl-N'-(1-cyano-3-methylthio) propylurea.

6. A composition in accordance with claim 1 wherein said compound is N-(α-naphthyl)N'-(-b 1-cyano-3-methylthio) propylurea.

7. A composition in accordance with claim 1 wherein said compound is N-phenyl-N'-(1-cyano-3-methylthio) propylurea.

8. A method for regulating plant growth comprising applying to a plant a growth-regulating effective amount of a compound of the formula

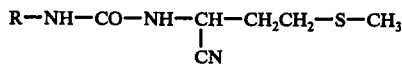

where R is H, alkyl of 1 – 5 carbons, naphthyl, phenyl or chlorinated phenyl with the proviso that R is not 3,5-dichlorophenyl.

9. A method in accordance with claim 8 wherein R is phenyl of chlorinated phenyl.

10. A method in accordance with claim 9 wherein R is phenyl or 3,4-dichlorophenyl.

11. A method in accordance with claim 8 wherein said compound is selected from the group consisting of
  N-methyl - N' - (1-cyano, 3 methylthio)propylurea;
  N-phenyl-N' - (1-cyano, 3 methylthio) propylurea;
  N 3,4 dichlorophenyl-N' (1-cyano, 3 methylthio)-propylurea; and
  N- (αnaphthyl) N' (1-cyano, 3 methylthio)-propylurea.

12. A method in accordance with claim 11, said compound consisting of N-(alpha-naphthyl)-N'-(1-cyano,3-methylthio) propylurea.

* * * * *